United States Patent [19]

Ams et al.

[11] Patent Number: 5,116,343

[45] Date of Patent: May 26, 1992

[54] DEVICE FOR DISINTEGRATING CONCRETIONS DISPOSED IN BODY CAVITIES

[75] Inventors: Felix Ams, Kämpfelbach; Ulf Zanger, Bruchsal; Ulrich Bolg, Sulzfeld, all of Fed. Rep. of Germany

[73] Assignee: Richard Wolf GmbH, Knittlingen, Fed. Rep. of Germany

[21] Appl. No.: 574,333

[22] Filed: Aug. 28, 1990

[30] Foreign Application Priority Data

Oct. 3, 1989 [DE] Fed. Rep. of Germany ....... 3932966

[51] Int. Cl.⁵ .......................................... A61B 17/22
[52] U.S. Cl. .................. 606/128; 51/59 SS; 604/22
[58] Field of Search ............. 128/24 AA; 606/127, 606/128; 604/22; 51/59 SS

[56] References Cited

U.S. PATENT DOCUMENTS

| | | | |
|---|---|---|---|
| 3,035,126 | 5/1962 | Crownover | 179/100.41 |
| 3,698,051 | 10/1972 | Miller | 29/25.35 |
| 3,817,141 | 6/1974 | Simonetti | 51/59 SS |
| 3,823,717 | 7/1974 | Polhman et al. | 606/128 |
| 3,830,240 | 8/1974 | Antonevich et al. | 128/328 |
| 4,156,863 | 5/1979 | Madison et al. | 340/9 |
| 4,178,935 | 12/1979 | Gekhman et al. | 606/128 |
| 4,535,759 | 8/1985 | Polk et al. | 128/24 AA |
| 4,660,573 | 4/1987 | Brumbach | 606/128 |
| 4,721,107 | 1/1988 | Borg et al. | 606/128 |
| 4,731,019 | 3/1988 | Martin | 51/59 SS |
| 4,816,018 | 3/1989 | Parisi | 128/24 AA |
| 4,823,793 | 4/1989 | Angulo et al. | 606/128 |
| 4,907,572 | 3/1990 | Borodulin et al. | 606/128 |
| 4,974,581 | 12/1990 | Wiksell | 128/24 AA |
| 4,978,333 | 12/1990 | Broadwin et al. | 51/59 SS |

FOREIGN PATENT DOCUMENTS

| | | | |
|---|---|---|---|
| 0209468 | 1/1987 | European Pat. Off. | 606/128 |
| 2219790 | 11/1974 | Fed. Rep. of Germany . | |
| 2733019 | 1/1979 | Fed. Rep. of Germany . | |
| 3826414 | 2/1989 | Fed. Rep. of Germany . | |
| 1225764 | 4/1986 | U.S.S.R. | 51/59 SS |
| 1264938 | 10/1986 | U.S.S.R. | 128/24 AA |

*Primary Examiner*—Lee S. Cohen
*Assistant Examiner*—K. M. Pfaffle
*Attorney, Agent, or Firm*—Panitch Schwarze Jacobs & Nadel

[57] ABSTRACT

A device is disclosed for the disintegration of concretions in body cavities. The device comprises at least one piezoelectric transducer element, for connection to a generator. The transducer element is connected between a reflector and a horn. Ultrasonic waves generated by the transducer element are directed by means of a sonotrode, to a concretion to be destroyed. At least the horn is provided with surface depressions which do not run parallel to its axis of symemtry, for the generation of transverse and rotational oscillations.

6 Claims, 1 Drawing Sheet

DEVICE FOR DISINTEGRATING CONCRETIONS DISPOSED IN BODY CAVITIES

FIELD OF THE INVENTION

The invention relates to a device for disintegrating concretions disposed in body cavities. The device comprises a transducer element disposed between a reflector and a horn, from which ultrasonic waves generated by the transducer element are directed to a concretion to be disintegrated.

BACKGROUND OF THE INVENTION

For the removal of a concretion from the interior of the body of a living creature, it may often be necessary first to break up the concretion, in order then to be able to remove it simply, for example by means of a suction device. Devices and methods based on the use of ultrasonic energy are often used for such disintegration. In this case disintegration of the concretion can be effected by means of instruments and equipment which operate with, or, without, contact with the concretion.

Those instruments which operate with contact with the concretion are usually equipped with a sonotrode in the form of a rod or tube, which is brought up to the concretion to be destroyed and is set in oscillation by an ultrasonic transducer. Because of the rod-like or tubular structure of the sonotrode, breaking up of a concretion is effected substantially by mechanical longitudinal oscillations transmitted thereto so that the concretion is merely pierced and the sonotrode must therefore, be applied at various sites on the concretion in order to achieve its complete destruction. The disintegration of the concretion is therefore prolonged, thereby increasing the stress on the patient.

DE-A-2219790 discloses a tubular ultrasonic oscillator equipped at its distal end with a loosely coupled rebound body provided with teeth intended to cause a hard concretion to burst by fracture. The time needed to cause the concretion to burst is, however, still too long because substantially only longitudinal oscillations are employed for disintegrating the concretion.

A device for the breaking down concretions in the ureter, by the application of a complex action by ultrasonic vibration and electrohydraulic shocks to the concretion is described in the DE-A-2733019. The sonotrode consists of a wire, the distal end of which is provided with teeth. The wire can also be provided at its distal end with longitudinal projections and grooves. For the transmission of ultrasonic vibration to the concretion, the distal end of the sonotrode is set in longitudinal and transverse oscillation by means of an ultrasonic transducer. The concretion is thus broken down under a regular milling action. The sonotrode is then exchanged for a probe, with which the concretion is further broken down according to the principle of electrohydraulic lithotripsy. The application of this device is extremely complicated and, therefore, time-consuming. Also, the use of electrohydraulic lithotripsy involves the risk that when the concretion bursts, the surrounding tissue is injured by the resulting fragments; diseases may consequentially develop.

A further device for the disintegration of urinary calculi is described in U.S. Pat No. 3,830,240. In this case also, it is proposed to disintegrate the concretion by means of a wire sonotrode. The sonotrode may be of different shape both at its connection piece to the transducer and also at its distal end, so that longitudinal and transverse oscillations can be produced at said distal end. By reason of the shape of the wire sonotrode at both its distal and its proximal regions, the sonotrode is very easily broken when in operation, with consequent injury to the surrounding tissue.

SUMMARY OF THE INVENTION

The present invention is intended to provide a device for disintegrating concretions with increased rapidity.

According to the present invention, in a device for the disintegration of concretions disposed in body cavities and comprising a transducer element arranged between a reflector and a horn, from which ultrasonic waves produced by the transducer element are directed to a concretion to be destroyed; the horn is provided with depressions on its surface, extending in a non-parallel manner with respect to its axis.

By virtue of said depressions which do not run parallel to the axis of symmetry of the horn, transverse and rotational oscillations are generated in addition to longitudinal oscillations, whereby the concretion to be disintegrated is very rapidly broken up.

This effect can be increased by providing the sonotrode with slits at its distal end, which do not run parallel to the axis of symmetry of the sonotrode and the length of which slits is approximately $\lambda/4$, where $\lambda$ corresponds to the wave lengths of the transverse oscillations. Sheets of the sonotrode material defined between adjacent ones of said slits can be additionally provided with indentations.

If the horn and/or the reflector of the device are of asymmetrical shape, further transverse and rotational oscillations can be generated, which contribute to the rapid breaking up of the concretion. Such asymmetrical shape can be produced, for example, by milled out, areal recesses on one side of the device.

For conducting said transverse and rotational oscillations generated by virtue of the profiling of the horn and/or reflector, as well as said longitudinal oscillations, in an optimum manner to the tip of the sonotrode, the sonotrode and the horn preferably consist of materials having a substantially identical acoustic impedance. Titanium has proved to be particularly suitable as a material for the horn and the sonotrode. Similarly, the horn may be of duralumin and the sonotrode of titanium.

DETAILED DESCRIPTION OF THE INVENTION

Figure 1:
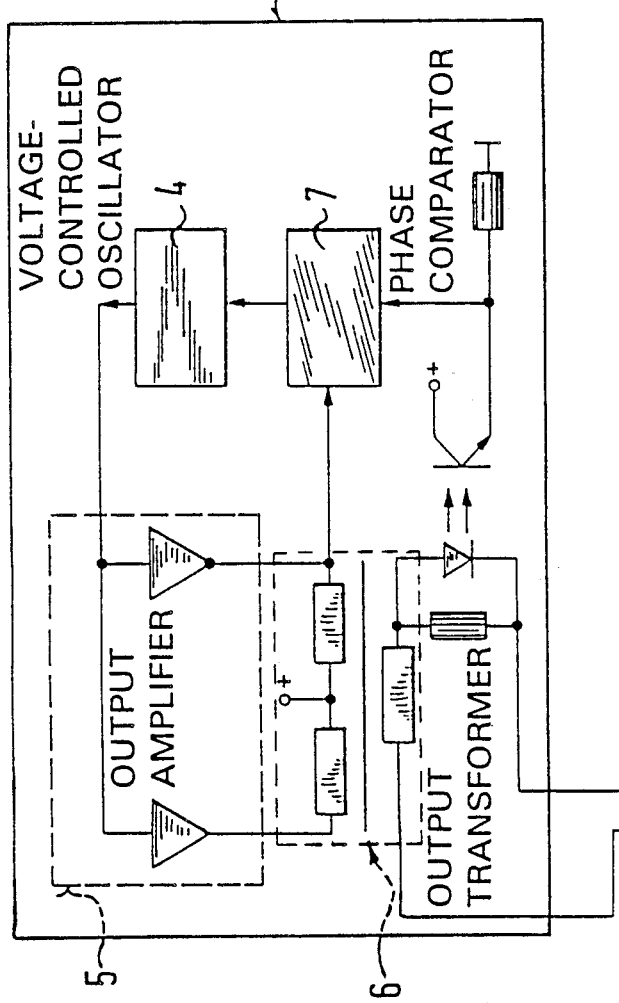
FIG. 1 is a diagrammatic side view of an embodiment of a disintegration device according to the invention, an associated ultrasonic generator therefor being shown block schematically.

The device for the disintegration of concretions disposed in body cavities, comprises at least one piezoelectric transducer 2 for connection to an ultrasonic generator 1, the transducer 2 being shown as consisting of two piezoceramic discs 10. The discs 10 are enclosed between a reflector 8 and a horn 9. Detachably connected to the horn 9 is a sonotrode 13, through which ultrasonic waves generated by the transducer 2 are directed to a concretion 11 which is to be disintegrated.

Since the ultrasonic generator 1 is of known type it will be described only briefly herein. For generating an electrical oscillation, the generator 1 essentially comprises a voltage-controlled oscillator 4, the output signal of which is passed to the transducer 2 by way of an output amplifier 5 and an output transformer 6. A phase comparator 7 compares the phases of the output voltage and of the output current of the output transformer 6 to produce a control voltage which is passed to the oscillator 4 in order to control it.

The electrical signal generated by the ultrasonic generator 1 is passed to the ultrasonic transducer 2 and is converted by the latter into mechanical oscillations. The sonotrode 13 is, in the present example, of tubular shape. The sonotrode 13 has a cavity which extends up to its proximal end, and is continued through the ultrasonic transducer 2 up to a suction connection 17. Suction out, of stone fragments, and if applicable, flushing fluid, can be carried out, by way of the said cavity.

Figure 2:
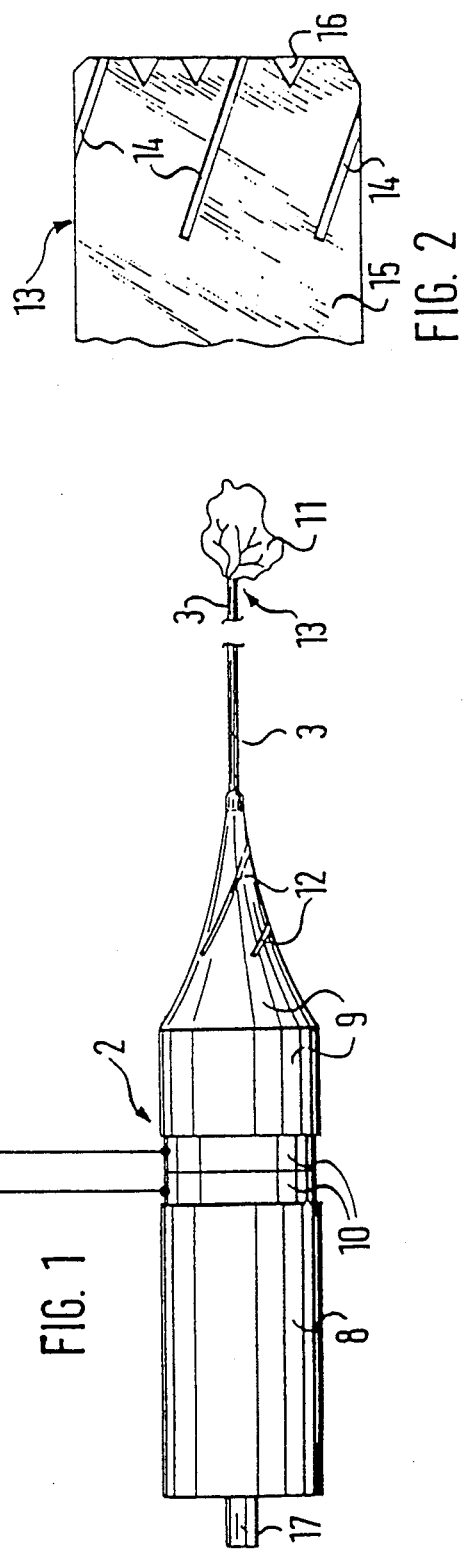
FIG. 2 is the enlarged side view of the distal end of a sonotrode of the device shown in FIG. 1.

In order to produce a high proportion of rotational and transverse oscillations, depressions 12 are milled in on the horn 9 of the ultrasonic transducer 2, so that they do not run parallel to the axis of symmetry of the horn 9. The same end is served by slits 14 formed in the distal end of the sonotrode 13 as shown in FIG. 2. The slits 14 are so arranged that they do not run parallel to the axis of symmetry of the sonotrode 13. The length of the slits 14 is approximately a quarter of the wave length of the generated transverse oscillations. The slits 14 are sufficiently narrow to ensure that an adequate suction effect is maintained through the sonotrode 3.

The sheet material 15 between adjacent slits 14 is provided with teeth or indentations 16, which augment the milling effect of the sonotrode tip.

For the additional generation of transverse and rotational oscillations, the horn 9 and/or the reflector 8 may be shaped asymmetrically, which can be achieved, for example, by milling out areal sections (not shown) on one side of the device.

Optimum transfer of energy between the ultrasonic transducer 2 and the sonotrode 3 towards the concretion 11 is achieved, in particular, if the sonotrode 3 and the horn 9 of the ultrasonic transducer 2, consist of the same material, or at least, of materials having substantially the same acoustic impedance. Thus the horn 9 may be made for example from duralumin or titanium, and the sonotrode 3 from titanium. By the use of titanium instead of the conventionally used fine steel as the material for the sonotrode 3, higher oscillation amplitudes can be achieved, thereby to reduce disintegration time of the concretion. The use of such material, also results in a considerable reduction in thermal losses.

What is claimed is:

1. A device for disintegrating concretions disposed in body cavities, the device comprising:
   a reflector;
   a horn having a longitudinal axis
   an ultrasonic transducer element connected between the reflector and the horn; and
   a sonotrode connected to the horn for directing ultrasonic waves generated by said transducer element to a concretion to be disintegrated;
   wherein the horn is provided with surface depression means which extend transversely of the longitudinal axis for generating transverse and rotational oscillations in addition to longitudinal oscillations.

2. A device as claimed in claim 1, wherein the sonotrode is provided at a distal end thereof with slits extending transversely of its axis of symmetry, the length of each slit being approximately $\lambda/4$, where $\lambda$ is the wave length of the transverse oscillations generated by said surface depression means.

3. A device as claimed in claim 2, wherein the sonotrode comprises sheets of material and wherein said material is provided with indentations between said slits.

4. A device as claimed in claim 1, wherein the sonotrode and the horn are made of material having substantially the same acoustic impedance.

5. A device as claimed in claim 4, wherein the horn and the sonotrode are made of titanium.

6. A device as claimed in claim 4, wherein the horn is made of duralumin and the sonotrode is made of titanium.

* * * * *